(12) United States Patent
Ishii et al.

(10) Patent No.: US 10,626,070 B2
(45) Date of Patent: Apr. 21, 2020

(54) DEVICE FOR MANUFACTURING ORGANIC SUBSTANCE AND METHOD FOR MANUFACTURING ORGANIC SUBSTANCE

(71) Applicant: SEKISUI CHEMICAL CO., LTD., Osaka (JP)

(72) Inventors: Tetsuya Ishii, Ibaraki (JP); Yoji Fujimori, Ibaraki (JP); Satoshi Koma, Tokyo (JP); Kazumi Okada, Ibaraki (JP); Kanetomo Satou, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/311,909

(22) PCT Filed: Jun. 21, 2017

(86) PCT No.: PCT/JP2017/022904
§ 371 (c)(1),
(2) Date: Dec. 20, 2018

(87) PCT Pub. No.: WO2017/221987
PCT Pub. Date: Dec. 28, 2017

(65) Prior Publication Data
US 2019/0202763 A1    Jul. 4, 2019

(30) Foreign Application Priority Data

Jun. 21, 2016    (JP) .................................. 2016-122454

(51) Int. Cl.
*C07C 29/152* (2006.01)
*B01D 3/14* (2006.01)
(Continued)

(52) U.S. Cl.
CPC ............ *C07C 29/152* (2013.01); *B01D 3/146* (2013.01); *B01D 53/04* (2013.01); *B01D 53/047* (2013.01);
(Continued)

(58) Field of Classification Search
CPC . B01D 3/00; B01D 3/14; B01D 3/143; B01D 3/146; B01D 53/00; B01D 53/02;
(Continued)

(56) References Cited

U.S. PATENT DOCUMENTS 4,971,606 A     11/1990  Sircar et al.
8,163,809 B2 *   4/2012  Chaubey ................ B01D 53/75
                                                252/373

FOREIGN PATENT DOCUMENTS

CA      2 923 022      3/2015
EP      3 176 148      6/2017
(Continued)

OTHER PUBLICATIONS

International Search Report dated Jul. 18, 2017 in International (PCT) Application No. PCT/JP2017/022904.
(Continued)

*Primary Examiner* — Natasha E Young
(74) *Attorney, Agent, or Firm* — Wenderoth, Lind & Ponack, L.L.P.

(57) ABSTRACT

A device for manufacturing an organic substance, including: a synthesis gas generation unit for generating a synthesis gas; an impurity concentration reducing unit including an adsorbent which is capable of adsorbing impurities contained in the synthesis gas, and produces a purified gas by contact of the adsorbent with the synthesis gas; an organic substance synthesis unit for producing an organic substance-containing solution from the purified gas as a raw material; an extraction unit for extracting the organic substance by
(Continued)

heating the organic substance-containing solution; a heating unit for preparing heated gas to be fed to the adsorbent; and a heat supplying unit which supplies the extraction unit with heat of the heated gas fed from the heating unit to the adsorbent.

9 Claims, 5 Drawing Sheets

(51) Int. Cl.
    *B01D 53/04*     (2006.01)
    *B01D 53/14*     (2006.01)
    *C10K 1/06*     (2006.01)
    *C10K 1/20*     (2006.01)
    *C10G 7/00*     (2006.01)
    *B01D 53/047*     (2006.01)
    *C10K 1/08*     (2006.01)
    *C07C 29/151*     (2006.01)

(52) U.S. Cl.
    CPC ..... *B01D 53/0438* (2013.01); *B01D 53/0462* (2013.01); *B01D 53/14* (2013.01); *C07C 29/1518* (2013.01); *C10K 1/08* (2013.01); *C10K 1/20* (2013.01); *B01D 2257/7027* (2013.01); *Y02P 20/57* (2015.11)

(58) Field of Classification Search
    CPC ................ B01D 53/04; B01D 53/0407; B01D 53/0438; B01D 53/0462; B01D 53/047; B01D 53/14; B01D 2257/00; B01D 2257/70; B01D 2257/702; B01D 2257/7027; C07C 29/00; C07C 29/15; C07C 29/151; C07C 29/1516; C07C 29/1518; C07C 29/152; C10G 7/00; C10K 1/00; C10K 1/08; C10K 1/20; Y02P 20/00; Y02P 20/50; Y02P 20/57
    See application file for complete search history.

(56) References Cited

FOREIGN PATENT DOCUMENTS

| | | |
|---|---|---|
| JP | 2004-085099 | 3/2004 |
| JP | 2016-059296 | 4/2016 |
| WO | 2016/017549 | 2/2016 |

OTHER PUBLICATIONS

Extended European Search Report dated Nov. 28, 2019 in European Patent Application No. 17815455.5.

* cited by examiner

DEVICE FOR MANUFACTURING ORGANIC SUBSTANCE AND METHOD FOR MANUFACTURING ORGANIC SUBSTANCE

This application is a national stage application claiming priority to PCT/JP2017/022904, now WO2017/221987, filed on Jun. 21, 2017, which claims priority to Japanese Patent Application Serial No. JP 2016-122454, filed on Jun. 21, 2016.

TECHNICAL FIELD

The present invention relates to a device and a method for manufacturing an organic substance from a synthesis gas.

Priority is claimed on Japanese Patent Application No. 2016-122454, filed Jun. 21, 2016, the contents of which are incorporated herein by reference.

BACKGROUND ART

Recently, vigorous studies have been made on methods for producing organic substances such as ethanol by subjecting a synthesis gas containing carbon monoxide and hydrogen, such as waste derived gas, coal gas, natural gas, petroleum exhaust gas or the like, to microbial fermentation using gas-utilizing bacteria. Particularly drawing attention from all over the world as an important technology for realizing the future recycling society is a method that produces organic substances using, as a raw material, a synthesis gas obtained by partially oxidizing a carbon source generally collected as waste, because such a method enables a production of organic substances without consuming newly obtained petroleum resources or edible resources.

However, the synthesis gas contains many impurities derived from raw materials, as well as carbon monoxide and hydrogen. If a synthesis gas containing a large amount of impurities is supplied to microorganisms as it is, the impurities adversely affect the microorganisms contained in the synthesis gas, which may kill the microorganisms or decrease the utilization rate of the microorganisms. It is known that, for avoiding such disadvantage, it is necessary to reduce components that adversely affect microorganisms through an impurity concentration reducing step before supplying the synthesis gas to the microorganisms.

Specifically, a temperature swing adsorption (TSA: Temperature Swing Adsorption) method and a pressure swing adsorption (PSA: Pressure Swing Adsorption) method are known as means for removing impurities contained in the synthesis gas to reduce the concentration thereof (Patent Documents 1 and 2). In these adsorption methods, impurities are adsorbed on the adsorbent and removed.

DESCRIPTION OF PRIOR ART

Patent Document

Patent Document 1: Japanese Unexamined Patent Application Publication No. 2004-85099
Patent Document 2: Japanese Unexamined Patent Application Publication No. 2016-59296

DISCLOSURE OF INVENTION

Problems to be Solved by the Invention

The present inventors have found that the organic substance production apparatuses as described in Patent Document 1 or Patent Document 2 which are configured to perform an impurity concentration reducing step consume large amount of thermal energy for removing impurities adsorbed on an adsorbent. The term "energy" in the present specification means resources used for utilities, such as heat and electricity.

The present inventors have found that an organic substance production method using microbial fermentation consumes extremely large amount of thermal energy for removing water in an extraction step of purifying an organic substance by distilling an aqueous solution containing an organic substance produced by microorganisms.

Therefore, contrary to its intended purpose, the organic substance production method utilizing microbial fermentation sometimes has a greater adverse effect on the global environment, as compared to known methods for producing organic substances derived from petroleum or organic substances derived from edible resources.

The present invention has been made in view of the above circumstances, and it is an object of the present invention to improve the energy efficiency of a device and a method for manufacturing an organic substance from a synthesis gas.

Means to Solve the Problems

As a result of intensive studies to solve the above problems, the inventors of the present invention have found that the above problem can be solved by reusing the heat, which has been used for desorbing impurities from the adsorbent used in the impurity concentration reducing step to regenerate the adsorbent, in the extraction step.

The present invention includes the embodiments described in the following [1] to [9].

[1] A device for manufacturing an organic substance, including:
a synthesis gas generation unit for generating a synthesis gas;
an impurity concentration reducing unit comprising an adsorbent which is capable of adsorbing impurities contained in the synthesis gas, and produces a purified gas by contact of the adsorbent with the synthesis gas;
an organic substance synthesis unit for producing an organic substance-containing solution from the purified gas as a raw material;
an extraction unit for extracting the organic substance by heating the organic substance-containing solution;
a heating unit for preparing heated gas to be fed to the adsorbent; and
a heat supplying unit which supplies the extraction unit with heat of the heated gas fed from the heating unit to the adsorbent.

[2] The device according to [1], wherein the organic substance-containing solution contains water, and the organic substance is ethanol.

[3] The device according to [1] or [2], wherein the extraction unit comprises a distillation device.

[4] The device according to [3], wherein the distillation device is a multi-effect distillation device.

[5] The device according to any one of [1] to [4], wherein the heat supplying unit has a heat exchanger.

[6] The device according to any one of [1] to [5], wherein the synthesis gas generation unit has a device for partially oxidizing a carbon source to generate a synthesis gas containing carbon monoxide and an impurity.

[7] The device according to [6], wherein the impurity is at least one compound selected from the group consisting of benzene, toluene, ethylbenzene, and xylene.

[8] A method for manufacturing an organic substance, including:
a synthesis gas generation step of generating a synthesis gas;
an impurity concentration reducing step of contacting the synthesis gas with an adsorbent capable of adsorbing impurities contained in the synthesis gas, thereby reducing an impurity concentration of the synthesis gas to obtain a purified gas;
an organic substance synthesis step of producing an organic substance-containing solution from the purified gas as a raw material; and
an extraction step of extracting the organic substance by heating the organic substance-containing solution,
wherein the method further comprises a desorption step of bringing a heated gas into contact with the adsorbent used in the impurity concentration reducing step to desorb impurities from the adsorbent, and
wherein heat of the heated gas having gone through the desorption step is recovered and reused in the extraction step.

[9] The method according to [8], wherein the extraction step is a step of distilling the organic substance-containing solution.

Effect of the Invention

The device and method for manufacturing an organic substance according to the present invention enables manufacturing of an organic substance with high energy efficiency.

DESCRIPTION OF THE EMBODIMENTS

Hereinbelow, an embodiment of the organic substance manufacturing device of the present invention and an embodiment of the organic substance manufacturing method of the present invention are described. However, these embodiments are only examples. Various alterations such as addition, omission and substitution of any components, etc. may be made as long as such alterations do not deviate from the gist of the present invention. The present invention should not be limited by the embodiments described below and is limited only by the annexed claims.

First Embodiment

[Organic Substance Manufacturing Device]

Figure 1:
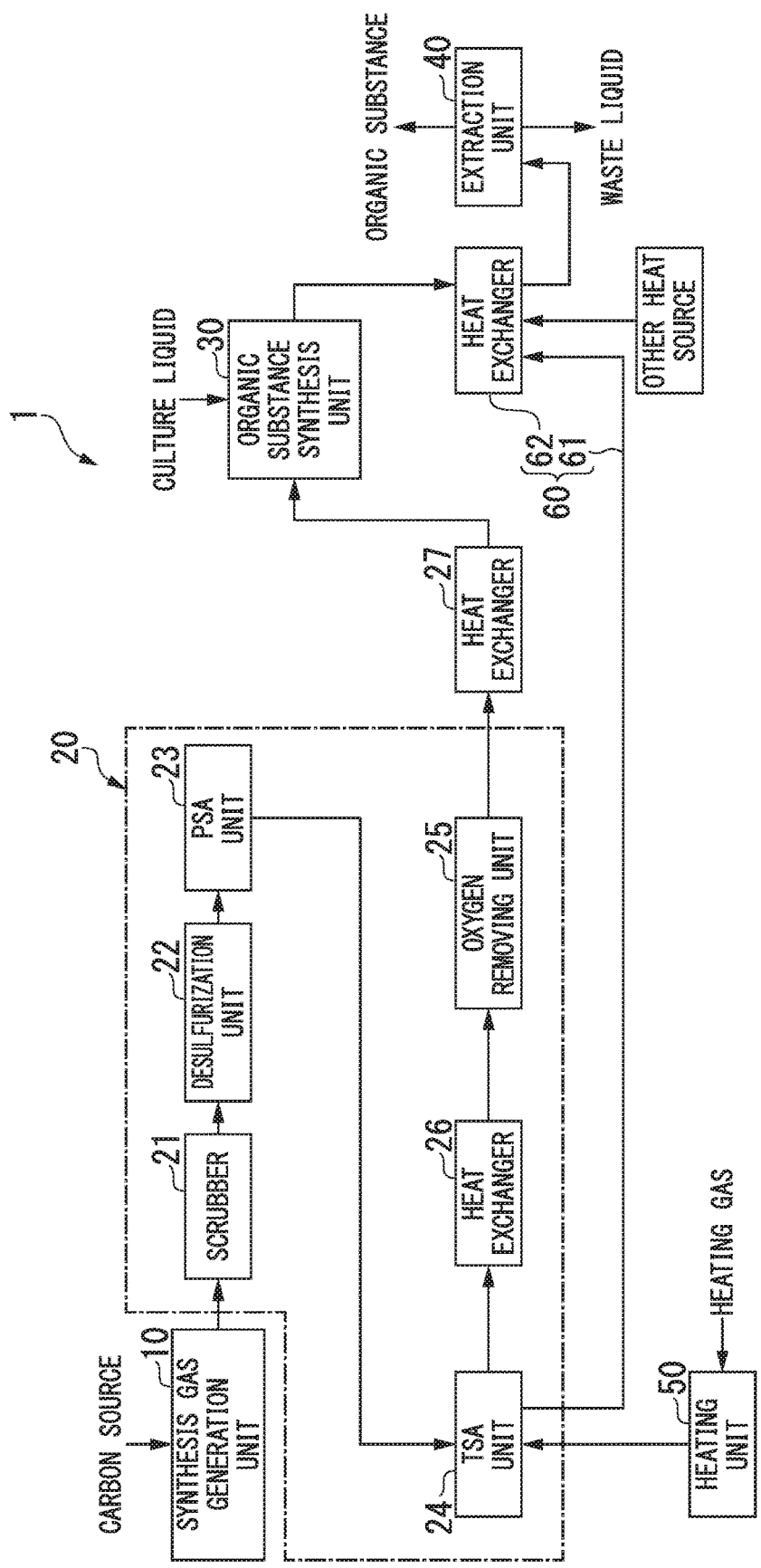
FIG. 1 is a schematic view of the device for producing an organic substance according to a first embodiment of the present invention.

As shown in FIG. 1, the organic substance manufacturing device 1 of the present embodiment includes: a synthesis gas generation unit 10, an impurity concentration reducing unit 20, an organic substance synthesis unit 30, an extraction unit 40, a heating unit 50, and a heat supplying unit 60.

<Synthesis Gas Generation Unit>

The synthesis gas generation unit 10 is a device for performing partial oxidation of a carbon source to generate a synthesis gas, and is not particularly limited as long as it is a reactor that allows a reaction between the carbon source and oxygen.

Examples of the carbon source include waste generally referred to as "trash" or "garbage" (household waste, industrial waste, waste plastic, etc.), biomass resources, coal, natural gas, petroleum and the like.

The synthesis gas generation unit 10 is preferably a gasification furnace for waste because it is advantageous for environmental protection and high concentration of carbon monoxide in the resulting synthesis gas.

The synthesis gas in the present invention is not particularly limited as long as it contains raw materials for synthesizing an organic substance of interest, but a gas containing at least one of carbon monoxide and hydrogen is preferable, and a gas containing both of carbon monoxide and hydrogen is more preferable.

The synthesis gas generated by the synthesis gas generation unit 10 usually contains impurities. The "impurities" contained in the synthesis gas means substances other than components normally contained in the air such as oxygen, nitrogen, carbon monoxide, hydrogen, carbon dioxide, water, and the like.

Specific examples of the impurities include soot, tar, benzene, toluene, ethylbenzene, xylene, ethane, ethylene, acetylene, naphthalene, acetamide, hydrogen cyanide, acetonitrile, acrylonitrile, methyl chloride, carbon disulfide, thiophene, methanethiol and the like, which are by-produced during the gasification process of the carbon source.

Of the impurities, those which are by-produced during the gasification process of waste are aromatic compounds (aromatic hydrocarbons) such as benzene, toluene, ethylbenzene and xylene; saturated hydrocarbons such as ethane; unsaturated hydrocarbons such as ethylene and acetylene; amide compounds such as acetamide; and sulfur compounds such as carbon disulfide. In addition, these by-products have cytotoxicity against microorganisms. Therefore, when the synthesis gas contains impurities having cytotoxicity against microorganisms, it is preferred to reduce the impurities in the synthesis gas before introducing the synthesis gas into the organic substance synthesis unit 30. Therefore, the total concentration of impurities in the synthesis gas is usually reduced to 100 ppm or less, preferably 10 ppm or less, more preferably 1 ppm or less.

The manufacturing device 1 of the present embodiment is particularly suitable when the impurity is at least one compound selected from the consisting of benzene, toluene, ethylbenzene, and xylene.

The impurities can be measured by a conventionally known measuring means such as a gas chromatography apparatus, a mass spectrometer, a gas chromatography-mass spectrometer, a secondary ion mass spectrometer, an atomic absorption spectrometer, a Raman spectrometer, a Fourier transform infrared spectrometer or the like.

<Impurity Concentration Reducing Unit>

The impurity concentration reducing unit 20 in the present embodiment has at least an adsorption device provided with adsorbent. Either a single adsorption device or multiple adsorption devices may be used. Further, it is preferable to provide two or more of the same adsorption devices such that adsorption and desorption can be concurrently carried out.

The adsorbent used in the adsorption device is a material that is capable of adsorbing impurities by using at least one of the adsorption action and the absorption action to thereby reduce impurities. Due to the adsorption ability of the adsorbent, impurities are adsorbed or absorbed by the adsorbent when the adsorbent and the synthesis gas come into contact, whereby the impurity concentration in the synthesis gas after contacting is reduced, and a purified gas with less impurities can be obtained.

Specifically, the impurity concentration reducing unit 20 in the present embodiment includes a scrubber 21, a desulfurization unit 22, a pressure swing adsorption unit 23 (hereinafter referred to as "PSA unit 23") and a temperature swing adsorption unit 24 (hereinafter referred to as "TSA unit 24"), an oxygen removing unit 25, and a heat exchanger 26.

The scrubber 21 is connected to the synthesis gas generation unit 10, and is provided with a means for reducing the concentration of water-soluble impurities contained in the synthesis gas. The scrubber 21 may be a device that captures water-soluble impurities in a wet manner, or may be a device that captures water-soluble impurities in a dry manner. For capturing water-soluble impurities, it is possible to use at least one of an adsorbent that adsorb water-soluble impurities, an absorbent that absorbs water-soluble impurities, a means that can structurally capture water-soluble impurities, and the like.

The desulfurization unit 22 is connected to the scrubber 21, and is provided with a means for removing the sulfur component contained in the synthesis gas. For example, the desulfurization unit 22 may be configured to include iron oxide or the like functioning as a scavenger for sulfur components in the container.

Between the desulfurization unit 22 and the PSA unit 23, a dehydration unit for removing moisture contained in the synthesis gas may be included. As a dehydrating agent to be used in the dehydration unit 22, silica gel or the like is usually used. If the dehydration unit is included as described above, moisture subsequently reacts with the adsorbent of the PSA unit 23 and the TSA unit 24, whereby the adsorption amount tends to be prevented from decreasing.

The PSA unit 23 is connected to the desulfurization unit 22 and includes a pressure swing adsorption device having an adsorbent. In the PSA unit 23, impurities contained in the synthesis gas can be reduced by the pressure swing adsorption method. Examples of impurities that can be reduced by the PSA unit 23 include aromatic hydrocarbons such as benzene, toluene, and xylene; saturated hydrocarbons such as ethane; unsaturated hydrocarbons such as ethylene and acetylene.

The TSA unit 24 is connected to the PSA unit 23 and includes a temperature swing adsorption device having an adsorbent. In the TSA unit 24, impurities contained in the synthesis gas can be reduced by the temperature swing adsorption method. Examples of the impurities that can be reduced by the PSA unit 24 include aromatic hydrocarbons such as benzene, toluene, and xylene; saturated hydrocarbons such as ethane; unsaturated hydrocarbons such as ethylene and acetylene.

As the TSA unit 24 in the present embodiment, for example, one having a first container and a second container, each filled with an adsorbent, can be mentioned. In the case of a TSA unit 24 having two containers, the synthesis gas is supplied to the first container that is used for removing impurities in the synthesis gas, while a heated gas to be described later is supplied to the second container to perform treatment to regenerate the adsorbent. Due to the use of two containers, removal of impurities and regeneration of adsorbent can be performed concurrently, whereby the impurities in the synthesis gas can be continuously removed without stopping the supply of the synthesis gas from the synthesis gas generation unit 10.

Further, regarding the TSA unit 24, for example, by providing the TSA unit 24 with three or more containers each filled with an adsorbent, it becomes possible to perform the regeneration process of the adsorbent for longer time, thereby improving the adsorption capacity. Also, when the first container is in the adsorption mode and the second container is in the regeneration mode, the third container can be left to the maintenance work such as replacement of the adsorbent.

The adsorbent used for the PSA unit 23 and the TSA unit 24 can be appropriately selected for the above impurities. Specific examples of the adsorbent include adsorbents such as porous silica, zeolite, and activated carbon; absorbents such as $K_2CO_3$ aqueous solution and amine solution; and solid absorbents such as an amine-modified porous silica. Among these adsorbents, activated carbon is preferable because it has high adsorption ability to aromatic hydrocarbons such as benzene and can be regenerated readily by heating.

The oxygen removing unit 25 is configured to include a catalyst for removing oxygen contained in the synthesis gas in the container. In the synthesis gas that has passed through the oxygen removing unit 25, the oxygen concentration is reduced. In addition, the oxygen removing unit 25 may be configured to reduce an acetylene concentration as well as the oxygen concentration. Further, the oxygen removing unit 25 may have a function of hydrogenating unsaturated hydrocarbons such as acetylene contained in the synthesis gas that has reached the oxygen removing unit 25.

The heat exchanger 26 is disposed between the TSA unit 24 and the oxygen removing unit 25 and is a heating means for heating the synthesis gas delivered from the TSA unit 24. Since the oxygen removing part 25 including a catalyst for removing oxygen functions at a high temperature of, for example, 150° C. or higher, the synthesis gas supplied to the oxygen removing unit 25 is heated by the heat exchanger 26 by heat exchange with the heating medium.

As described above, the oxygen removing unit 25 using the catalyst operates at a high temperature of, for example, 150° C. or higher. Therefore, a high-temperature synthesis gas is supplied to the oxygen removing unit 25, and oxygen reacts with hydrogen and carbon monoxide in the oxygen removing unit 25, which results in temperature rise of the synthesis gas up to about 200° C. Accordingly, the synthesis gas discharged from the oxygen removing unit 25 also has a high temperature. However, if a high-temperature gas is directly supplied to the organic substance synthesis unit 30, the gas-utilizing bacteria may be killed.

Therefore, in the present embodiment, a heat exchanger 27 is provided between the oxygen removing unit 25 and the organic substance synthesis unit 30. The temperature of the synthesis gas can be lowered by this heat exchanger 27. As a result, a synthesis gas having a low temperature of, for example, 100° C. or less can be supplied from the heat exchanger 27 to the organic substance synthesis unit 30. Therefore, by providing the heat exchanger 27, it is possible to suppress death of microorganisms in the organic substance synthesis unit 30.

<Organic Substance Synthesis Unit>

The organic substance synthesis unit 30 is not particularly limited as long as it can produce an organic substance-containing solution containing an organic substance using the purified gas containing the synthesis gas as a raw material, but the organic substance synthesis unit 30 is preferably provided with a fermentation tank having a gas-utilizing bacterium.

When the organic substance synthesis unit 30 includes such a fermentation tank, a culture liquid containing the gas-utilizing bacteria is supplied to the fermentation tank together with the synthesis gas.

The organic substance to be produced in the organic substance synthesis unit 30 is not particularly limited. Examples of the organic substance include alcohols, organic acids, fatty acids, fats and oils, ketones, biomass, sugars, formic acid, lactic acid and the like. More specific examples of the organic substance include methanol, ethanol, butanol, isopropyl alcohol, 2,3-butanediol, acetic acid, lactic acid, isoprene and the like. Among the above organic substances, an organic substance containing ethanol is preferable from the viewpoint of high yield and low energy consumption. The use of the organic substance to be produced is not particularly limited, and it can be used as raw materials for resins and the like, cosmetics, beverages, chemical substances, and can also be used as various fuels.

The gas-utilizing bacteria used in the present embodiment are microorganisms capable of producing organic substances by fermentation using a synthesis gas as a nutrient, and may be eubacteria or archaebacteria.

Examples of the eubacteria include bacteria of the genus *Clostridium*, bacteria of the genus *Moorella*, bacteria of the genus *Acetobacterium*, bacteria of the genus *Carboxydocella*, bacteria of the genus *Rhodopseudomonas*, bacteria of the genus *Eubacterium*, bacteria of the genus *Butyribacterium*, bacteria of the genus *Oligotropha*, bacteria of the genus *Bradyrhizobium*, bacteria of the genus *Ralsotonia* which is an aerobic hydrogen oxidizing bacterium, and the like.

Examples of the archaebacteria include those belonging to the genera *Methanobacterium, Methanobrevibacter, Methanocalculus, Methanococcus, Methanosarcina, Methanosphaera, Methanothermobacter, Methanothrix, Methanoculleus, Methanofollis, Methanogenium, Methanospirillium, Methanosaeta, Thermococcus, Thermofilum, Arcaheoglobus* and the like.

Among the archaebacteria, those belonging to the genera *Methanosarcina, Methanococcus, Methanothermobacter, Methanothrix, Thermococcus, Thermofilum* and *Archaeoglobus* are preferable. Further, from the viewpoint of utilization of carbon monoxide and carbon dioxide, those belonging to the genera *Methanosarcina, Methanothermobactor* and *Methanococcus* are more preferable, and those belonging to the genera *Methanosarcina* and *Methanococcus* are particularly preferable.

Specific examples of the archaea belonging to the genus *Methanosarcina* include *Methanosarcina barkeri, Methanosarcina mazei, Methanosarcina acetivorans* and the like.

Bacteria with a high ability to produce an organic substance of interest are appropriately selected and used from among the gas-utilizing bacteria as described above.

For example, when ethanol is produced as the organic substance in the organic substance synthesis unit 30, *Clostridium autoethanogenum, Clostridium ljungdahlii, Clostridium aceticum, Clostridium carboxidivorans, Moorella thermoacetica, Acetobacterium woodii* or the like, which have high ethanol producing ability, are used as the gas-utilizing bacteria.

The manufacturing device 1 of the present embodiment is particularly suitable when the organic substance generated in the organic substance synthesis unit 30 is ethanol and the obtained organic substance-containing solution contains water.

As the microorganism for producing alcohol such as ethanol from the synthesis gas, those belonging to the genus *Clostridium* are preferred. When a medium is contained in the organic substance synthesis unit 30, specific examples of liquid contained in the medium include, for example, water and the like.

<Extraction Unit>

The extraction unit 40 is connected to the organic substance synthesis unit 30, and extracts a target organic substance from the organic substance-containing solution to purify the organic substance. Examples of the extraction unit 40 include a distillation device, a treatment device including a pervaporation membrane, a treatment device including a zeolite dehydration membrane, a treatment device for removing low-boiling substances (water or the like) having a boiling point lower than that of the organic substance, a treatment device for removing high-boiling substances having a boiling point higher than that of the organic substance, a treatment device including an ion exchange membrane, and the like. Among these, the extraction unit 40 is preferably one provided with a distillation device, since the organic substance can be easily extracted and such an extraction unit is suitable for recycling heat. As the distillation device, it is more preferable to use a multi-effect distillation device because it can easily reduce the amount of heat required for distillation of the organic substance-containing solution supplied from the organic substance synthesis unit 30, and has high energy efficiency. As the multi-effect distillation device, those having a dual effect distillation section can be mentioned.

Further, the extraction unit 40 may be a temperature swing adsorption device (TSA device) having an adsorbent for adsorbing organic substances or an absorbent for absorbing organic substances. The TSA device constituting the extraction unit 40 is a device provided separately from the TSA unit 24 constituting the impurity concentration reducing unit 20.

<Heating Unit>

The heating unit 50 is a device in which a heated gas to be supplied to the adsorbent is prepared.

In the above TSA unit 24, impurities are adsorbed by the adsorbent and removed, so that as the operation time of the organic substance manufacturing device 1 becomes long, the adsorption amount of impurities in the adsorbent gradually decreases, eventually reaching the adsorption saturation. Therefore, it is necessary to desorb the adsorbed impurities at the time when the adsorption amount has decreased to a certain extent. In the present embodiment, by heating the adsorbent, impurities adsorbed in the adsorbent are desorbed so as to regenerate the adsorbent. The heating unit 50 is provided with a heating means for heating the heating gas, and is a device for generating a heated gas for heating the adsorbent and supplying it to the adsorbent.

The heating gas can be prepared by heating a heating gas composed of air, an inert gas such as nitrogen or argon, or a mixed gas thereof. As the heated gas prepared by heating the heating gas, a nitrogen gas, a noble gas and superheated steam are preferable because these are easy to handle, and a nitrogen gas and superheated steam are more preferable from the viewpoint of cost.

As a heating means for heating the heating gas, an electric heater, a combustion furnace or the like may be used, or exhaust heat or the like in an electric furnace, a boiler, a gasification furnace or the like may be used as well.

<Heat Supplying Unit>

The heat supplying unit 60 is a means that provides the extraction unit 40 with the heat of the heated gas fed to the adsorbent from the heating unit 50.

Specifically, the heat supplying unit 60 includes a pipe leading the high temperature gas used for regenerating the adsorbent to the extracting unit 40, a heat exchanger, or the like, and one provided with a heat exchanger is preferable for the following reason. The heat supplying unit 60 in the present embodiment includes a pipe 61 connected to the TSA unit 24 and a heat exchanger 62 connected to the pipe 61.

The heated gas after contacting the adsorbent contains the desorbed impurities. If the heated gas containing the impurities is simply brought into contact with the organic material-containing solution, there is a risk that the desorbed impurities may be mixed into the organic substance and extracted together with the organic substance. When the heat supplying unit 60 has a heat exchanger and exchanges the heat of the heated gas to a heating medium supplied to the extraction unit 40, it is not necessary to bring the heated gas into contact with the organic substance-containing solution, whereby it is possible to prevent the impurities from being mixed into the organic substance-containing solution.

There is no particular limitation on the heating medium to be transferred to the extractor 40 via the heat exchanger as long as it is a generally used heating medium such as superheated steam, various gases, high boiling point liquid (metal sodium, etc.), but a nitrogen gas is preferable.

[Organic Substance Manufacturing Method]

The organic substance manufacturing method of the present embodiment includes a synthesis gas generation step, an impurity concentration reducing step, an organic substance synthesis step, and an extraction step, to thereby produce an organic substance.

The organic substance manufacturing method of the present embodiment further includes a desorption step of bringing a heated gas into contact with the adsorbent used in the impurity concentration reducing step to desorb impurities from the adsorbent, wherein heat of the heated gas having gone through the desorption step is recovered and reused in the extraction step.

<Synthesis Gas Generation Step>

The synthesis gas generation step is a step of generating a synthesis gas. More specifically, this step is a step of performing partial oxidation of the aforementioned carbon source to generate a synthesis gas.

As a method for the partial oxidation of the carbon source, for example, a method of burning the carbon source under a condition where the amount of oxygen is stoichiometrically less than the carbon amount of the carbon source can be mentioned.

As the synthesis gas, a gas containing at least one of carbon monoxide and hydrogen is preferable, and a gas containing both carbon monoxide and hydrogen is more preferable. In addition, the synthesis gas obtained by the synthesis gas generation step contains impurities mainly derived from the carbon source as well as carbon monoxide and hydrogen.

<Impurity Concentration Reducing Step>

The impurity concentration reducing step is a step of contacting the synthesis gas with an adsorbent capable of adsorbing impurities contained in the synthesis gas, thereby reducing an impurity concentration of the synthesis gas to obtain a purified gas.

In the impurity concentration reducing step in the present embodiment, first, the synthesis gas supplied from the synthesis gas generation unit 10 is passed through the scrubber 21 to reduce the concentration of water-soluble impurities contained in the synthesis gas. Subsequently, the gas passed through the scrubber 21 is passed through the desulfurization unit 22 to remove the sulfur component contained in the synthesis gas.

Then, the gas passed through the desulfurization unit 22 is passed through the PSA unit 23 and further passed through the TSA unit 24 to remove hydrocarbon impurities. In the PSA unit 23 and the TSA unit 24, the hydrocarbon impurities are captured in a state of being adsorbed or absorbed by the adsorbent and removed.

In the PSA unit 23, for allowing the impurities in the synthesis gas to be adsorbed by the adsorbent, the synthesis gas is supplied so as to have a pressure equal to or higher than normal pressure, whereas, for allowing the impurities to be desorbed from the adsorbent, the atmosphere surrounding the adsorbent is depressurized.

In the TSA unit 24, for allowing the impurities in the synthesis gas to be adsorbed by the adsorbent, the temperature of the adsorbent is lowered, whereas, for allowing the impurities to be desorbed from the adsorbent, the temperature of the adsorbent is increased.

When the TSA unit 24 has the first container and the second container, each filled with the adsorbent, it is possible to supply the synthesis gas from the PSA unit 23 to the first container to remove impurities from the synthesis gas. Simultaneously with the above, a heated gas can be supplied from the heating unit 50 to the second container so as to heat and regenerate the adsorbent. Therefore, when the TSA unit 24 has the two containers, the impurities in the synthesis gas can be continuously removed without stopping the supply of the synthesis gas from the synthesis gas generation step.

The synthesis gas passed through the TSA unit 24 is allowed to pass through the heat exchanger 26 and heated to, for example, 150° C. or higher, preferably 250° C. or higher, and fed to the oxygen removing unit 25. In the oxygen removing unit 25, the synthesis gas contacts the catalyst for removing oxygen to thereby remove oxygen. Thus, the oxygen concentration in the synthesis gas can be reduced.

When the oxygen removing unit 25 is configured to be capable of removing acetylene, the concentration of acetylene in the synthesis gas can be reduced by passing the synthesis gas through the oxygen removing unit 25.

When the oxygen removing unit 25 is configured to be capable of hydrogenating unsaturated hydrocarbons, the unsaturated hydrocarbons in the synthesis gas can be hydrogenated and converted into saturated hydrocarbons by passing the synthesis gas through the oxygen removing unit 25.

In the oxygen removing unit 25, the gas temperature may rise due to the reaction of oxygen with hydrogen or carbon monoxide, and the degree of temperature rise of the gas depends on the oxygen concentration of the synthesis gas.

In the impurity concentration reducing step, the amount of impurities to be removed is usually 10% by mass or more, preferably 30% by mass or more, more preferably 50% by mass or more, more preferably 80% by mass or more, particularly preferably 95% by mass or more, most preferably 98% by mass or more, based on the total amount of impurities in the synthesis gas before being fed into the impurity concentration reducing unit 20. The removal of impurities by the impurity concentration reducing step tends to suppress the decrease in the utilization ratio of the gas-utilizing bacteria used in the subsequent organic substance synthesis step. Therefore, the yield of the organic substance can be improved.

<Desorption Step>

The desorption step is a step of desorbing impurities from the adsorbent to regenerate the adsorbent.

As described above, the adsorption amount of impurities by the adsorbent gradually decreases as the production time of the organic substance becomes longer. Therefore, in the present embodiment, when the adsorption amount has decreased to some extent, the adsorbent is heated to desorb the impurities adsorbed in the adsorbent to regenerate the adsorbent.

With respect to the desorption step in the present embodiment, there is no particular limitation as long as the heated gas is allowed to pass through the TSA unit 24 and can allow desorption of the impurities adsorbed in the adsorbent to occur. Specifically, a method may be adopted, in which the heated gas obtained in the heating unit 50 is fed to and contacted with the adsorbent being used in the TSA unit 24 to heat the adsorbent. Alternatively, the heating unit 50 and the TSA unit 24 may be combined to heat the TSA unit 24 to supply the heating gas. In this way, the impurities adsorbed in the adsorbent are desorbed to regenerate the adsorbent.

In the desorption step, the adsorbent may be depressurized simultaneously with heating. The depressurization with heating enables the impurities to be desorbed more easily.

While the heated gas is being fed to the adsorbent, the supply of the synthesis gas to the adsorbent is stopped.

The temperature of the heated gas sent to the adsorbent can be appropriately set depending on the temperature at which impurities are desorbed from the adsorbent, but is usually 60° C. or higher, preferably 100° C. or higher, more preferably 150° C. or higher, still more preferably 200° C. or higher, particularly preferably 300° C. or higher, most preferably 320° C. or higher. When the temperature of the heated gas is in the above range, impurities tend to be sufficiently desorbed from the adsorbent.

The contact time between the heated gas and the adsorbent is not particularly limited, but is usually 30 seconds or more, preferably 30 minutes or more, more preferably 1 hour or more, further preferably 4 hours or more, particularly preferably 8 hours or more. When the contact time between the heated gas and the adsorbent is in the above range, impurities tend to be sufficiently desorbed from the adsorbent.

<Organic Substance Synthesis Step>

The organic substance synthesis step is a step of producing an organic substance-containing solution from the purified gas as a raw material.

For example, in the organic substance synthesis step, an organic substance-containing solution containing an organic substance can be produced in the organic substance synthesis unit 30 by microbial fermentation using a gas-utilizing bacterium with the purified gas containing a synthesis gas as a nutrient.

<Extraction Step>

The extraction step is a step of extracting the organic substance by heating the organic substance-containing solution. Specifically, in the extraction step, the organic substance is extracted in the extraction unit 40 from the organic substance-containing solution supplied from the organic substance synthesis unit 30. For taking out the organic substance from the extraction unit 40, a step of heating the extraction unit 40 is performed.

For example, in the case of using a distillation device equipped with a distillation column in the extraction step, the organic substance-containing solution supplied from the organic substance synthesis unit 30 is distilled to take out the organic substance. For performing the distillation, the inside of the distillation column is heated.

When the TSA device is used in the extraction step, the organic substance-containing solution supplied from the organic substance synthesis unit 30 is allowed to be adsorbed by the adsorbent or absorbed by the absorbent, whereafter the TSA device is heated to desorb the organic substance from the adsorbent or absorbent and the organic substance is taken out.

By the extraction step as described above, the organic substance of high purity can be obtained by separating the organic substance from other substances.

For distilling the organic substance-containing solution in the extraction step, the temperature inside the distillation device is not particularly limited, but is usually 80° C. or higher, preferably 100° C. or higher. Particularly, when the organic substance-containing solution is an ethanol aqueous solution, the temperature inside the distillation device is usually 80° C. or higher, preferably 100° C. or higher.

The temperature inside the distillation device means a temperature at a position in the lower part of the distillation column or in the reboiler where the temperature is the highest. When a multi-effect distillation device is adopted, the temperature is usually 95° C. or higher, preferably 120° C. or higher, more preferably 140° C. or higher.

The temperature of a condenser used for condensing the gas vaporized by distillation is usually 60° C. or lower, preferably 40° C. or lower, more preferably 35° C. or lower. The lower the temperature of the condenser, the higher the recovery ratio, but a larger condenser is needed, which may necessitate the use of a chiller that consumes a large amount of electric power.

By setting the temperature inside the distillation device within the above range, it is possible to sufficiently distill the organic substance and to easily separate the organic substance of interest from other components (waste liquid), whereby the organic substance can be surely collected.

The pressure in the distillation device during the distillation of the organic substance is not particularly limited, but from the viewpoint of lowering the temperature of the heat source, the pressure is preferably less than the atmospheric pressure, more preferably about 60 to 95 kPa (gauge pressure). However, when a high-temperature heat source is available, the pressure inside the distillation device may be higher than the atmospheric pressure. The higher the pressure inside the distillation apparatus, the more easy the condensation of the organic substance; therefore, the organic substance of interest tends to be obtained in sufficient amount even without setting the temperature for condensation at an excessively low level. When the multi-effect distillation device is used, it is preferable that the distillation device is divided into a plurality of distillation zones, and different pressures are applied to the respective distillation zones.

By setting the pressure in the distillation device within the above range, the separation efficiency of the organic substance can be improved and the yield of the organic substance can be improved.

In the present embodiment, the heat of the heated gas having gone through the desorption step is recovered and used in the extraction step.

Specifically, the heated gas used for regenerating the adsorbent is introduced into the heat exchanger 62 through the pipe 61. In the heat exchanger 62, the organic substance-containing solution to be sent to the extraction step is heated. By using the heat exchanger 62, the heated gas supplied through the pipe 61 and the organic substance-containing solution can be heat-exchanged in a noncontact manner, thus enabling the heating of the organic substance-containing solution. Since the noncontact heat exchange prevents impurities contained in the heated gas from being mixed into the organic substance-containing solution, the organic substance having higher purity can be easily produced.

The temperature of the heated gas introduced into the heat exchanger 62 is usually 80° C. or higher, preferably 100° C. or higher, more preferably 150° C. or higher, furthermore preferably 300° C. or higher, particularly preferably 325° C. or higher.

<Effects>

In the organic substance manufacturing device 1 and the manufacturing method described above, the heat of the heated gas used for regenerating the adsorbent of the TSA unit 24 is recovered and reused in the extraction unit 40. Therefore, for heating the extraction unit 40, the amount of heat separately supplied from other heat source can be reduced.

Accordingly, the present embodiment can improve the energy efficiency in manufacturing of the organic substance from the synthesis gas. As a result, by using the manufacturing device 1, an organic substance can be produced at low cost.

The manufacturing device 1 and the manufacturing method of the present embodiment are particularly suitable in the case where a synthesis gas is generated from waste and ethanol is manufactured from the synthesis gas.

Second Embodiment

[Organic Substance Manufacturing Device]

Figure 2:
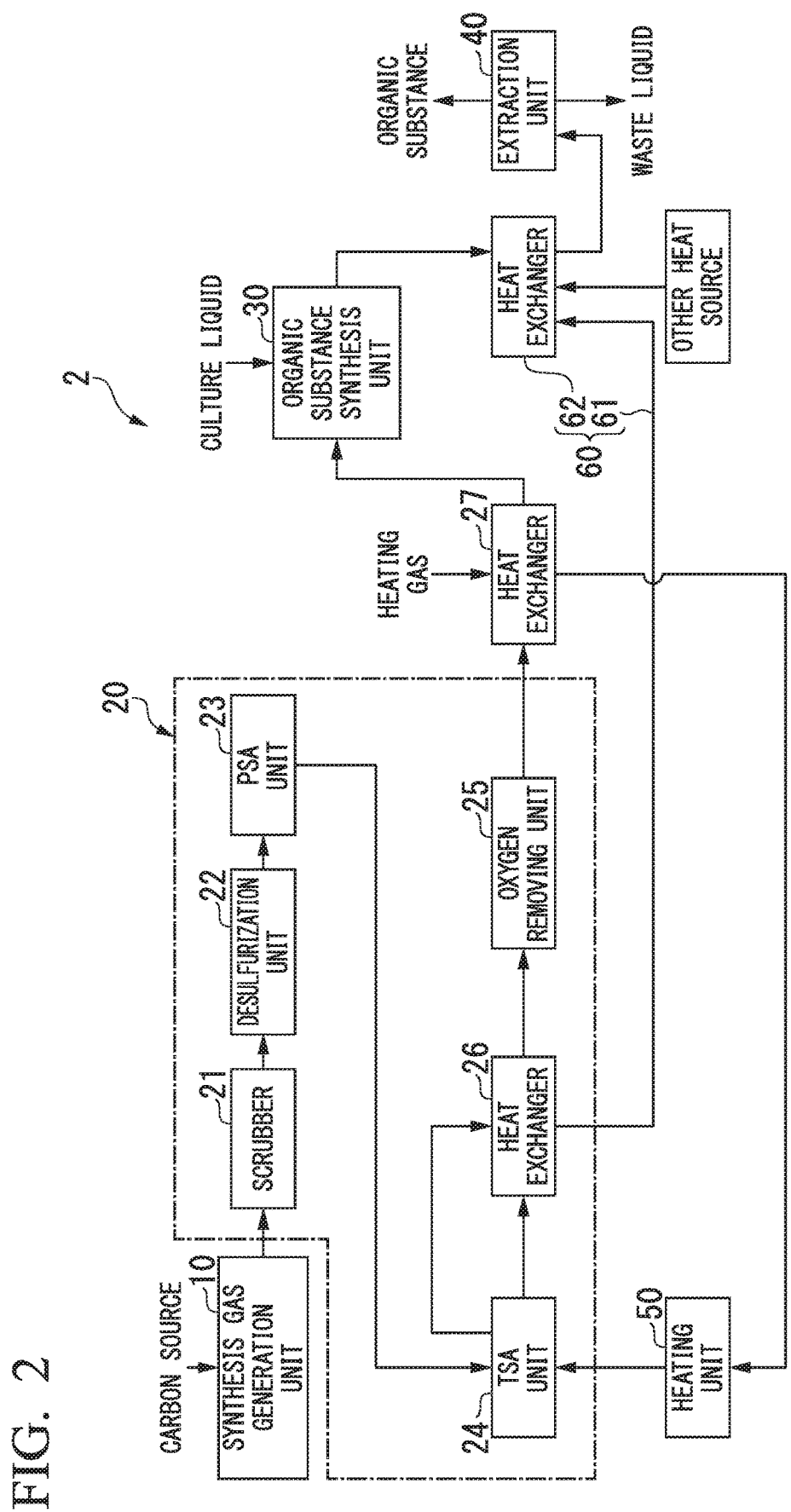
FIG. 2 is a schematic view of the device for producing an organic substance according to a second embodiment of the present invention.

As shown in FIG. 2, the organic substance manufacturing device 2 of this embodiment includes: a synthesis gas generation unit 10, an impurity concentration reducing unit 20, an organic substance synthesis unit 30, an extraction unit 40, a heating unit 50, and a heat supplying unit 60.

The manufacturing device 2 according to the second embodiment is different from the device according to the first embodiment in that the heated gas discharged from the TSA unit 24 passes through the heat exchanger 26, and is supplied to the heat exchanger 62 through the pipe 61 connected to the heat exchanger 62. Further, the manufacturing device 2 according to the second embodiment is different from the manufacturing device 1 according to the first embodiment also in that the heating gas is supplied to the heating unit 50 via the heat exchanger 27.

The heated gas discharged from the TSA unit 24 has a very high temperature of, for example, 250° C. or higher, preferably 300° C. or higher, more preferably 320° C. or higher. Therefore, in the manufacturing device 1 of the first embodiment, the difference in temperature between the heated gas sent to the heat exchanger 62 and the organic substance-containing solution supplied to the heat exchanger 62 is too large; therefore, it cannot be said that the heat exchange efficiency in the heat exchanger 62 is sufficiently high. In contrast, in the manufacturing device 2 of the present embodiment, the high-temperature heated gas discharged from the TSA unit 24 is caused to pass through the heat exchanger 26, whereby the temperature of the synthesis gas supplied to the oxygen removing unit 25 can be raised. At the same time, the heat exchange is performed between the heated gas and the synthesis gas in the heat exchanger 26, whereby the heated gas that has been cooled can be supplied to the heat exchanger 62.

Therefore, in the manufacturing device 2 of the present embodiment, the difference in temperature between the heated gas sent to the heat exchanger 62 and the organic substance-containing solution supplied to the heat exchanger 62 is decreased, whereby the heat exchange efficiency in the heat exchanger 62 can be improved. Thus, according to the manufacturing device 2 and the manufacturing method of the present embodiment, it is possible to further increase the energy efficiency in manufacturing the organic substance, and to further reduce the manufacturing cost of the organic substance.

Further, as in the manufacturing device 1 of the first embodiment, in order to directly supply the heating gas to the heating unit 50 and sufficiently raise the temperature in the heating unit 50, it is necessary to supply a large amount of energy to the heating unit 50. On the other hand, in the manufacturing device 2 of the present embodiment, it is possible to perform the heat exchange between the heating gas and the synthesis gas in the heat exchanger 27 to which the high-temperature synthesis gas is supplied, and then, feed the resulting preheated heating gas into the heating unit 50. Therefore, it is unnecessary to raise the temperature of the heating gas by using another heating device different from the manufacturing device 1, and a low temperature gas can be used as the heating gas.

Therefore, in the manufacturing device 2 of the second embodiment, energy required for heating the heating gas in the heating unit 50 can be reduced even when a low temperature gas is used as the heating gas. Thus, according to the manufacturing device 2 and the manufacturing method of the embodiment, it is possible to further increase the energy efficiency in manufacturing the organic substance, and it is possible to further reduce the manufacturing cost of the organic substance.

Other Embodiments

In the above embodiments, using the PSA unit and the TSA unit in combination, the synthesis gas treated by the PSA unit is then treated by the TSA unit; however, the present invention is not limited to such configuration. The organic substance manufacturing device of the present invention may have only the TSA unit. Further, for example, the organic substance manufacturing device of the present invention may have a TSA unit and a PSA unit connected on the downstream side of the TSA unit. That is, the synthesis gas may be treated with the PSA unit after being treated with the TSA unit.

Further, the organic substance manufacturing device of the present invention may be provided with multiple units with respect to at least one of the TSA unit and the PSA unit. In that case, the order of connection between the TSA unit and the PSA unit is not particularly limited, and for example, the PSA unit, the TSA unit and the PSA unit may be provided in this order from the upstream side along the flow of the synthesis gas.

Furthermore, the impurity concentration reducing unit used in the organic substance manufacturing method of the present invention need to have at least the TSA unit, whereas the scrubber and the desulfurization unit are optional constituents. The scrubber, the desulfurization unit and the PSA unit may be appropriately installed according to the type of impurities contained in the synthesis gas, the desired concentration of the organic substance, etc.

EXAMPLES

Comparative Example 1

Figure 3:
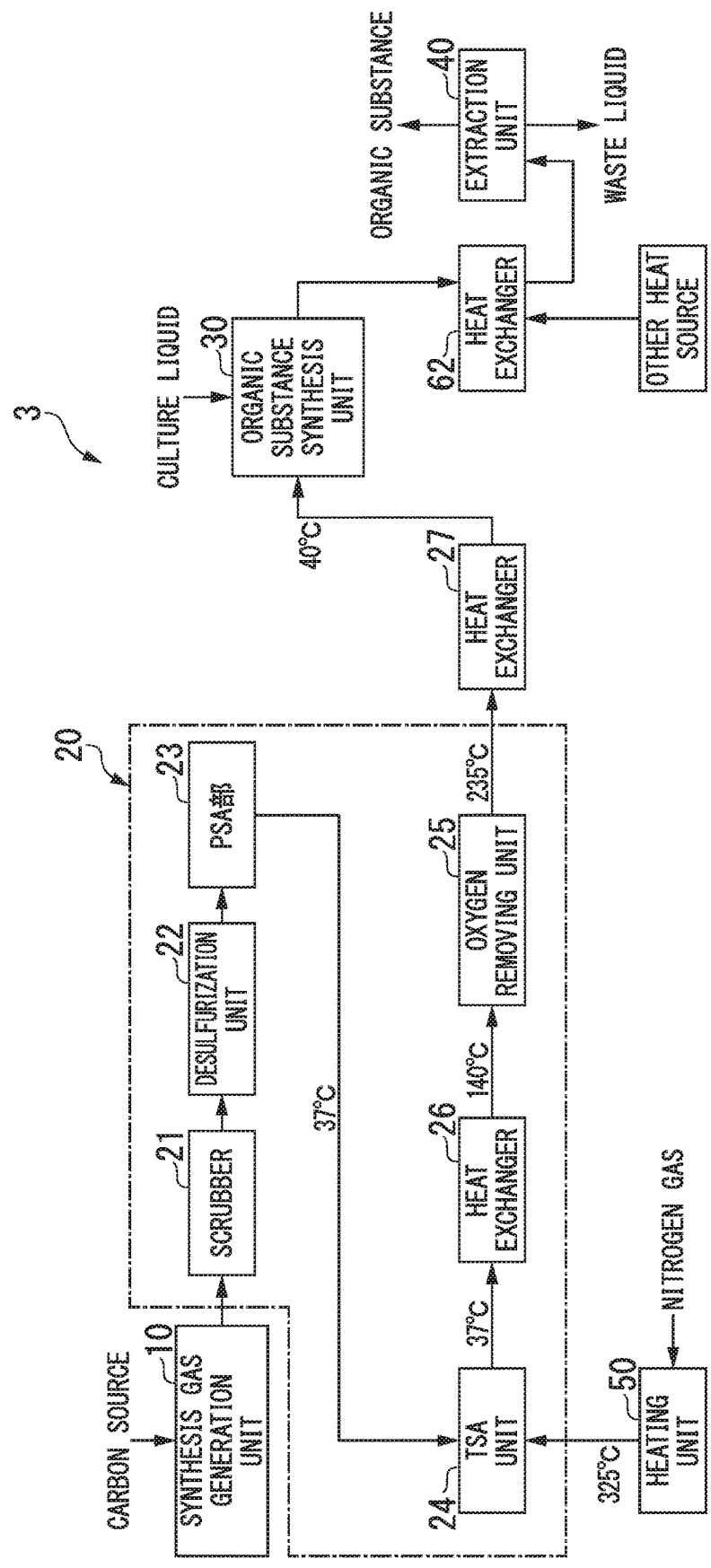
FIG. 3 is a schematic view of the device for producing an organic substance used in Comparative Example 1.

FIG. 3 shows an organic substance manufacturing device 3 used in Comparative Example 1. This organic substance manufacturing device 3 includes a synthesis gas generation unit 10, an impurity concentration reducing unit 20, an organic substance synthesis unit 30, an extraction unit 40 and a heating unit 50, and is the same as the organic substance manufacturing device of the first embodiment except that a heat supplying unit is not provided.

With respect to this manufacturing device 3, a simulation was conducted to produce ethanol from a synthesis gas for 24 hours under the following conditions. As a result, the amount of heat required for ethanol production was 5499 kW.

In the organic substance manufacturing method using the organic substance manufacturing device 3, first, a raw material waste was contacted in the synthesis gas generation unit 10 with an oxygen gas produced from the air by the cryogenic separation, whereby the carbon source contained in the raw material waste was partially oxidized to obtain a synthesis gas containing carbon monoxide, carbon dioxide, hydrogen and the like at 10000 Nm$^3$/h.

Next, the synthesis gas was passed through the scrubber 21, the desulfurization unit 22, and the PSA unit 23 to remove impurities. The amount of purified gas at the outlet of the PSA unit 23 was 7000 Nm$^3$/h.

Thereafter, the purified gas was passed through the TSA unit 24 and the oxygen removing unit 25, and then supplied to the organic substance synthesis unit 30 including a fermentation tank containing *Clostridium* bacteria. In the organic substance synthesis unit 30, an aqueous solution containing 5% by mass of ethanol was obtained as a result of fermentation using the synthesis gas as a raw material.

Then, a 5% by mass aqueous solution of ethanol was placed in the extraction unit 40 composed of a distillation column, and distilled until the concentration reached 92% by mass to obtain ethanol.

This simulation was performed based on the following premises: the oxygen removing unit 25 was set at 235° C., the extraction unit 40 was set at 100° C., and 7000 Nm$^3$ of a heated gas for regenerating the adsorbent in the TSA unit 24 (nitrogen gas from which oxygen had been removed by cryogenic separation) was heated to 325° C. and allowed to flow for 12 hours. Further, the TSA unit 24 was provided with a first container and a second container, each filled with an adsorbent. The simulation model of the TSA unit was configured to desorb impurities from the adsorbent in the second container when impurities in the synthesis gas are adsorbed by the adsorbent in the first container, and to desorb impurities from the adsorbent in the first container when impurities in the synthesis gas are adsorbed by the adsorbent in the second container.]

In FIG. 3, the temperatures of the gas obtained from the simulation are shown.

As a result of the simulation, the amount of heat used in the oxygen removing unit 25 was 260 kW, the amount of heat used for heating the nitrogen gas for regenerating the adsorbent in the TSA unit 24 was 378 kW, and the amount of heat used for distilling the ethanol aqueous solution in the extraction unit 40 was 4861 kW. Therefore, the total amount of heat required for producing ethanol from the synthesis gas was 5499 kW.

Example 1

Figure 4:
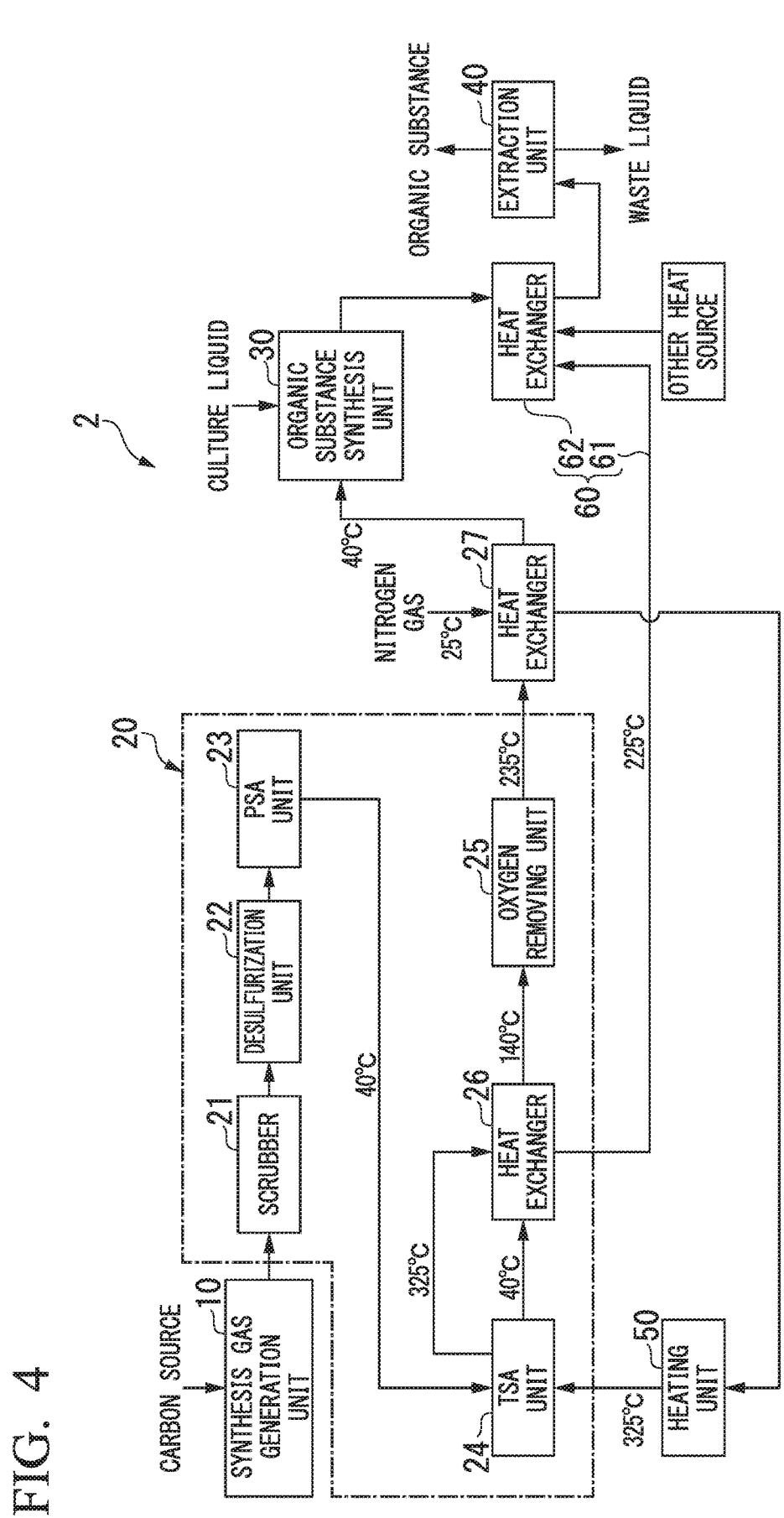
FIG. 4 is a schematic view of the device for producing an organic substance used in Example 1.

FIG. 4 shows an organic substance manufacturing device 2 used in Example 1. This organic substance manufacturing device 2 includes a synthesis gas generation unit 10, an impurity concentration reducing unit 20, an organic substance synthesis unit 30, an extraction unit 40, a heating unit 50 and a heat supplying unit 60, and is the same as the organic substance manufacturing device of the second embodiment.

With respect to this manufacturing device 2, a simulation was conducted to produce ethanol from a synthesis gas for 24 hours under the following conditions. As a result, the amount of heat required for ethanol production was 4967 kW.

The simulation in Example 1 is different from Comparative Example 1 in that the heat generated in the oxygen removing unit 25 was used for preheating the nitrogen gas, and that the heat of the heated nitrogen gas discharged from the TSA unit 24 was utilized for heating the synthesis gas supplied to the oxygen removing unit 25 and was utilized for heating the distillation column of the extraction unit 40 using the heat supplying unit 60. Other conditions were the same as in Comparative Example 1.

In FIG. 4, the temperatures of the gas obtained from the simulation are shown.

As a result of the simulation, the amount of heat used in the oxygen removing unit 25 was 0 kW, the amount of heat used for heating the nitrogen gas for regenerating the adsorbent in the TSA unit 24 was 257 kW, and the amount of heat used for distilling the ethanol aqueous solution in the extraction unit 40 was 4710 kW. Therefore, the total amount of heat required for producing ethanol from the synthesis gas was 4967 kW.

Thus, it has become clear that by supplying the heat of the nitrogen gas used for regenerating the adsorbent to the extraction unit by the heat supplying unit, it is possible to greatly reduce the amount of energy consumed in producing ethanol from the synthesis gas.

Example 2

Figure 5:
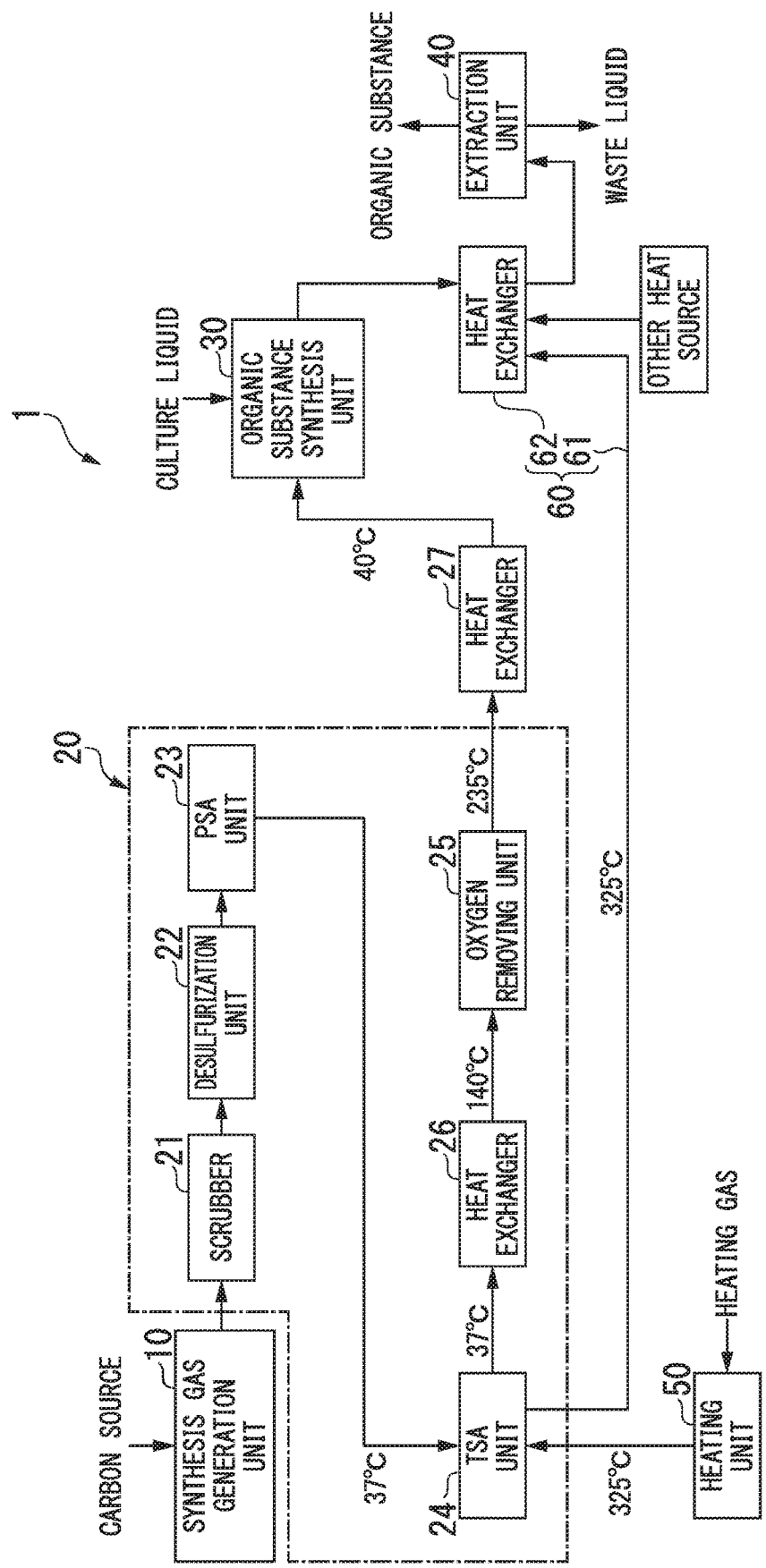
FIG. 5 is a schematic view of the device for producing an organic substance used in Example 2.

FIG. 5 shows an organic substance manufacturing device 1 used in Example 2. This organic substance manufacturing device 1 includes a synthesis gas generation unit 10, an impurity concentration reducing unit 20, an organic substance synthesis unit 30, an extraction unit 40, a heating unit 50 and a heat supplying unit 60, and is the same as the organic substance manufacturing device of the first embodiment. This manufacturing device 1 is the same as the manufacturing device 3 of Comparative Example 1 except that the manufacturing device 1 is provided with a pipe through which a heated gas passes between the TSA unit 24 and the heat exchanger 29.

With respect to this manufacturing device 1, a simulation was conducted to produce ethanol from a synthesis gas for 24 hours under the following conditions. As a result, the amount of heat required for ethanol production was 5121 kW.

The simulation in Example 2 is different from Comparative Example 1 in that the heat of the heated nitrogen gas discharged from the TSA unit 24 was utilized for heating the distillation column of the extraction unit 40 using the heat supplying unit 60. Other conditions were the same as in Comparative Example 1.

In FIG. 5, the temperatures of the gas obtained from the simulation are shown.

As a result of the simulation, the amount of heat used in the oxygen removing unit 25 was 260 kW, the amount of heat used for heating the nitrogen gas for regenerating the adsorbent in the TSA unit 24 was 378 kW, and the amount of heat used for distilling the ethanol aqueous solution in the extraction unit 40 was 4483 kW. Therefore, the total amount of heat required for producing ethanol from the synthesis gas was 5121 kW.

Thus, it has become clear that by supplying the heat of the nitrogen gas used for regenerating the adsorbent to the extraction unit by the heat supplying unit, it is possible to greatly reduce the amount of energy consumed in producing ethanol from the synthesis gas.

INDUSTRIAL APPLICABILITY

The device and method for manufacturing an organic substance according to the present invention enables manufacturing of an organic substance with high energy efficiency.

DESCRIPTION OF THE REFERENCE SIGNS 1,2: Manufacturing device
11: Synthesis gas generation unit
20: Impurity concentration reducing unit
21: Scrubber
22: Desulfurization unit
23: Pressure swing adsorption unit (PSA unit)
24: Temperature swing adsorption unit (TSA unit)
25: Oxygen removing unit
26: Heat exchanger
27: Heat exchanger
30: Organic substance synthesis unit
40: Extraction unit
50: Heating unit
60: Heat supplying unit
61: Pipe
62: Heat exchanger

The invention claimed is:

1. A device for manufacturing an organic substance, comprising:
   a synthesis gas generation unit for generating a synthesis gas;
   an impurity concentration reducing unit comprising an adsorbent which is capable of adsorbing impurities contained in the synthesis gas, and produces a purified gas by contact of the adsorbent with the synthesis gas;
   an organic substance synthesis unit for producing an organic substance-containing solution from the purified gas as a raw material;
   an extraction unit for extracting the organic substance by heating the organic substance-containing solution;
   a heating unit for preparing heated gas to be fed to the adsorbent; and
   a heat supplying unit which supplies the extraction unit with heat of the heated gas fed from the heating unit to the adsorbent.

2. The device according to claim 1, wherein the organic substance-containing solution contains water, and the organic substance is ethanol.

3. The device according to claim 1, wherein the extraction unit comprises a distillation device.

4. The device according to claim 3, wherein the distillation device is a multi-effect distillation device.

5. The device according to claim 1, wherein the heat supplying unit has a heat exchanger.

6. The device according to claim 1, wherein the synthesis gas generation unit has a device for partially oxidizing a carbon source to generate a synthesis gas containing carbon monoxide and an impurity.

7. The device according to claim 6, wherein the impurity is at least one compound selected from the group consisting of benzene, toluene, ethylbenzene, and xylene.

8. A method for manufacturing an organic substance, comprising:
   a synthesis gas generation step of generating a synthesis gas;
   an impurity concentration reducing step of contacting the synthesis gas with an adsorbent capable of adsorbing impurities contained in the synthesis gas, thereby reducing an impurity concentration of the synthesis gas to obtain a purified gas;
   an organic substance synthesis step of producing an organic substance-containing solution from the purified gas as a raw material; and
   an extraction step of extracting the organic substance by heating the organic substance-containing solution,
   wherein the method further comprises a desorption step of bringing a heated gas into contact with the adsorbent used in the impurity concentration reducing step to desorb impurities from the adsorbent, and
   wherein heat of the heated gas having gone through the desorption step is recovered and reused in the extraction step.

9. The method according to claim 8, wherein the extraction step is a step of distilling the organic substance-containing solution.

* * * * *